United States Patent [19]

Clark et al.

[11] Patent Number: 5,428,065
[45] Date of Patent: Jun. 27, 1995

[54] 1,3-BENZENEDIMETHANAMINES USEFUL AS CENTRAL NERVOUS SYSTEM ACTIVE AGENTS

[75] Inventors: Barry P. Clark, Froyle; Graham H. Timms, Camberley, both of United Kingdom

[73] Assignee: Lilly Industries Limited, Basingstoke, England

[21] Appl. No.: 312,600

[22] Filed: Sep. 27, 1994

[30] Foreign Application Priority Data

Sep. 29, 1993 [GB] United Kingdom ............... 9320051

[51] Int. Cl.[6] ............... A61K 31/135; A61K 31/155; C07C 211/28; C07C 279/12
[52] U.S. Cl. ............... 514/634; 514/654; 514/655; 558/422; 560/18; 560/34; 560/37; 560/42; 562/426; 562/439; 562/442; 562/451; 564/237; 564/368; 564/388
[58] Field of Search ............... 514/634, 654, 655; 564/237, 368, 388

[56] References Cited

U.S. PATENT DOCUMENTS 3,280,097 10/1966 Cizek ............... 564/368
3,755,445 8/1973 Manschke et al. ............... 564/368

FOREIGN PATENT DOCUMENTS 407032 1/1991 European Pat. Off. ... A61K 31/135
91/00853 1/1991 WIPO ............... C07C 211/13

OTHER PUBLICATIONS

Merck Index, 8699 (11th Ed., 1989), p. 1379.

*Primary Examiner*—Peter O'Sullivan
*Attorney, Agent, or Firm*—Robert A. Conrad; David E. Boone; Gerald V. Dahling

[57] ABSTRACT

Pharmaceutical compounds of the formula:

$R^1$ to $R^8$ are each hydrogen or $C_{1-4}$ alkyl, m, n and p are each 0, 1, or 2, q is 0, 1, 2 or 3, X and Z are each $C_{1-4}$ alkyl, $C_{1-4}$ alkoxy, hydroxy, nitro, cyano, halo, trihalomethyl, carboxy, $C_{1-4}$ alkoxy-carbonyl or phenyl, and in addition z, together with the phenyl ring to which it is attached, can be:

Y is —O—, —S— or —CH$_2$—, V is —(CH$_2$)$_r$— or —(CH$_2$)$_r$S— where r is 1 to 15, and W is hydrogen or optionally substituted phenyl; and salts thereof.

5 Claims, No Drawings

1,3-BENZENEDIMETHANAMINES USEFUL AS CENTRAL NERVOUS SYSTEM ACTIVE AGENTS

This invention relates to novel compounds having pharmaceutical properties.

The compounds of the invention are of the following general formula:

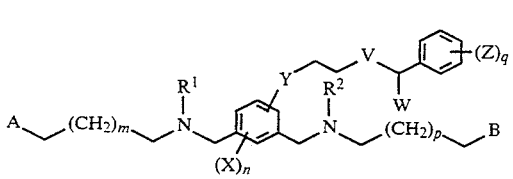
(I)

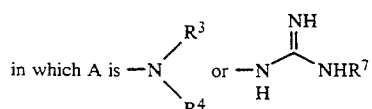

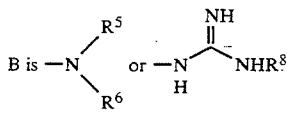

$R^1$ to $R^8$ are each hydrogen or $C_{1-4}$ alkyl, m, n and p are each 0, 1, or 2, q is 0, 1, 2 or 3, X and Z are each $C_{1-4}$ alkyl, $C_{1-4}$ alkoxy, hydroxy, nitro, cyano, halo, trihalomethyl, carboxy, $C_{1-4}$ alkoxy-carbonyl or phenyl, and in addition Z, together with the phenyl ring to which it is attached, can be:

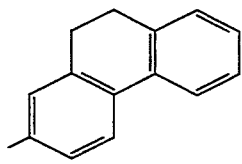

Y is —O—, —S— or —CH$_2$—, V is —(CH$_2$)$_r$— or —(CH$_2$)$_r$S— where r is 1 to 15, and W is hydrogen or optionally substituted phenyl; and salts thereof.

The compounds of the invention are indicated for use in the treatment of diseases of the central nervous system.

When reference is made to $C_{1-4}$ alkyl in the above formula, preferred groups are methyl, ethyl, propyl, isopropyl and tert.butyl. Especially preferred groups are methyl and ethyl. A $C_{1-4}$ alkoxy group is one such alkyl group linked via an oxygen atom. Preferred halo groups are fluoro, chloro and bromo, and trifluoromethyl is the preferred example of trihalomethyl.

It is preferred that A and B are —NR$^3$R$^4$ and —NR$^5$R$^6$ respectively, and that R$^3$, R$^4$, R$^5$ and R$^6$ are each hydrogen or methyl. Also it is preferred that R$^7$ and R$^8$ are both hydrogen. The groups R$^1$ and R$^2$ are preferably hydrogen, and both m and p are preferably 1. The value of n is preferably 0 or 1, and Y is preferably —O—.

An optionally substituted phenyl is preferably unsubstituted phenyl and can also be phenyl substituted with one or more substituents, preferably one or two substituents, selected from halo, preferably fluoro or chloro, trifluoromethyl, $C_{1-4}$ alkoxy, hydroxy, nitro, $C_{1-4}$ alkyl, $C_{1-4}$ alkylthio and carboxy.

The group V is preferably —(CH$_2$)$_r$—, and W is preferably hydrogen.

A preferred group of compounds is of the general formula:

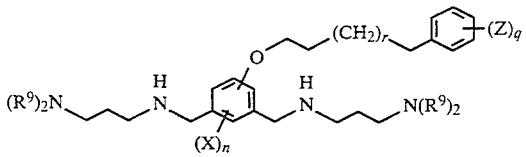

in which R$^9$ is $C_{1-4}$ alkyl, especially methyl, n is 0 or 1, X is $C_{1-4}$ alkyl, r is 3 to 10, Z is $C_{1-4}$ alkyl, $C_{1-4}$ alkoxy, hydroxy, nitro, cyano, halo, trihalomethyl, carboxy, $C_{1-4}$ alkoxycarbonyl or phenyl, and q is 0, 1 or 2; and salts thereof.

It will be understood that salts of the compounds of the invention can be prepared, and such salts are included in the invention. They can be any of the well known acid or base addition salts. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

In addition to pharmaceutically-acceptable salts, other salts are included in the invention. They may serve as intermediates in the purification of compounds or in the preparation of other, for example pharmaceutically-acceptable, salts, or are useful for identification, characterisation or purification.

It will be appreciated that the compounds of the invention can contain one or more asymmetric carbon atoms which give rise to isomers. The compounds are normally prepared as racemic mixtures and can conveniently be used as such, but individual isomers can be isolated by conventional techniques if so desired. Such racemic mixtures and individual optical isomers form part of the present invention.

The invention also comprises a process for producing a compound of formula (I) above, which comprises:

1) reacting a compound of the formula:

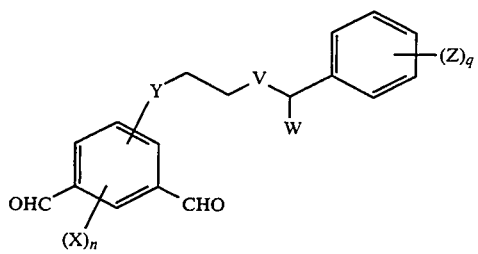

with a compound of the formula:

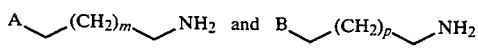

in which A and B are

and

respectively
to give a compound of formula (I) in which $R^1$ and $R^2$ are hydrogen, 2) reacting a compound of formula (I) in which A and B are —$NH_2$ with an amidinating agent to give a compound in which A or B is

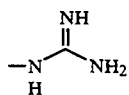

and 3) alkylating a compound of formula (I) in which $R^1$, $R^2$, $R^3$, $R^4$, $R^5$, $R^6$, $R^7$ or $R^8$ is hydrogen.

With regard to process variant (1), the reaction is preferably carried out in an organic solvent such as, for example, methanol, and preferably at a temperature of from 0° C. to 50° C.

The intermediates of formula (II) are novel and included as part of the invention. They can be prepared by well known methods. For example, compounds in which Y is oxygen can be prepared by reaction of an appropriate compound of formula:

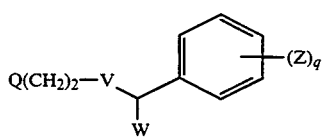

where Q is a leaving group such as for example a halogen atom, preferably chloro, or tosyl, with a compound of the formula:

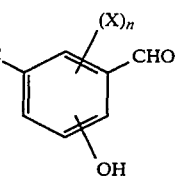

Intermediate compounds of formula (II) in which Y is sulphur can be prepared by reacting a compound of formula:

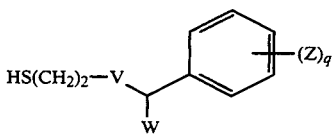

with a compound of formula:

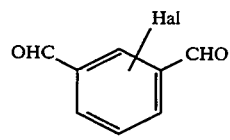

where Hal is a halogen atom, preferably bromo; and intermediates of formula (II) in which Y is —$CH_2$— can be prepared from methyl dicyanobenzene by reaction with a base such as, for example, lithium diisopropylamide and the appropriate halide, e.g iodide:

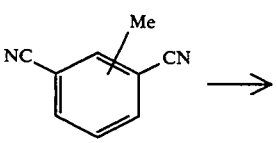

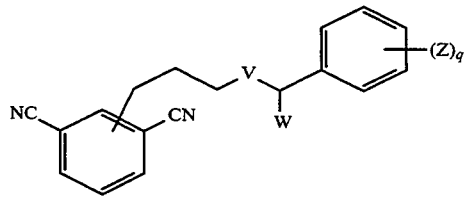

followed by reaction with a reduction agent such as, for example, diisobutylaluminium hydride to give the corresponding dialdehyde.

With regard to process variant (2), the reaction is preferably carried out in an organic solvent such as, for example, an aqueous/alcohol solvent, and preferably at a temperature of from 0° C. to 150° C. The amidinating agent can be a pyrazole carboxamidine, and is most preferably 3,5-dimethylpyrazole carboxamidine.

It will be appreciated that compounds of the invention in which one or more of $R^1$, $R^2$, $R^3$, $R^4$, $R^5$, $R^6$, $R^7$ or $R^8$ is hydrogen, can be alkylated to provide other compounds of formula (I) above.

As mentioned above, the compounds of the invention have useful central nervous system activity. For example, the compounds have been found to affect calcium ion uptake into cortical synaptosomes in a test based on that described by McMahon, R. T. and Nicholls, D. A., 1991, J. Neurochem, 56, 86–94. Compounds of the invention inhibit calcium uptake at concentrations of less than 10 μM.

The compounds of the invention are indicated for use in the treatment of diseases of the central nervous system, for example, in the treatment of neurological disorders such as acute neurodegenerative diseases, for example, stroke, cerebal ischemia and head and spinal cord trauma, and chronic neurodegenerative diseases such as, for example, Alzheimer's disease, Parkinson's disease, Amyotrophic lateral sclerosis, AIDS-induced dementia and Huntington's chorea. The compounds are also indicated for use in the treatment of psychotic conditions such as schizophrenia, schizophreniform diseases, acute mania and anxiety, or impairment of learning or memory.

The invention also includes a pharmaceutical composition comprising a pharmaceutically acceptable diluent or carrier in association with a compound of the invention, or a pharmaceutically acceptable salt or ester thereof.

The compounds may be administered by various routes, for example by the oral or rectal route, topically or parenterally, for example by injection or infusion, being usually employed in the form of a pharmaceutical composition. Such compositions are prepared in a manner well known in the pharmaceutical art and comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing, for example, up to 10% by weight of the compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydrobenzoate, talc magnesium stearate and mineral oil. The compositions of an injection may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the conditions to be treated, the choice of compound to be administered and the chosen route of administration, and therefore the above dosage ranges are not intended to limit the scope of the invention in any way.

This invention is illustrated by the following Examples.

EXAMPLE 1

5-Methyl-2-(8-phenyloctyloxy)-1,3-benzenedicarboxaldehyde

8-Phenyloctyl bromide (2.69 g, 10 mmol) was added to a stirred mixture of 5-methyl-2-hydroxy-1,3-benzenedicarboxaldehyde (1.64 g, 10 mmol) and anhydrous potassium carbonate (1.38 g, 10 mmol) in dry dimethylformamide (20 ml) at room temperature under nitrogen. The suspension was heated to 80° C. for 3 hours then allowed to cool. Water (40 ml) was added and the mixture extracted with diethyl ether (2×40 ml). The extracts were dried, filtered and evaporated to a yellow solid. Recrystallisation from methanol (25 ml) gave the title product as pale yellow crystals, m.p. 59° C.

EXAMPLE 2

N,N'-Bis(3-dimethylaminopropyl)-5-methyl-2-(8-phenyloctyloxy)-1,3-benzenedimethanamine, tetrahydrochloride A solution of 5-methyl-2-(8-phenyloctyloxy)-1,3-benzenedicarboxaldehyde (0.88 g, 2.5 mmol) and dimethylaminopropanamine (0.51 g, 5 mmol) in methanol (10 ml) was heated under reflux for 1 hour. After cooling to room temperature, solid sodium borohydride (0.76 g, 20 mmol) was added portionwise to the stirred solution over half an hour under nitrogen. The mixture was stirred overnight and then evaporated to a white semi-solid residue. Triturated with toluene (40 ml), the inorganic salts were filtered and the filtrate evaporated to a colourless oil (1.34 g). The crude product was purified by chromatography on flash silica eluting with 5% 0.880 ammonia in methanol to give the free base of the title product as an oil (0.92 g). The hydrochloride salt was prepared by adding ethanolic hydrogen chloride to an ethanol solution of the free base. Evaporation to dryness gave the title product as a hydroscopic foam (MS: M+H+ =525).

EXAMPLE 3

N,N'-Bis(3-dimethylaminopropyl)-N,N'-dimethyl-5methyl-2-(8-phenyloctyloxy)-1,3-benzenedimethanamine, tetrahydrochloride A solution of N,N'-bis(3-dimethylaminopropyl-5-methyl-2-(8-phenyloctyloxy)-1,3-benzenedimethanamine tetrahydrochloride (0.25 g, 0.37 mmol), 40% aqueous formaldehyde (0.2 ml), 95% formic acid (0.2 ml) and dimethylformamide (2 ml) was heated to 80° C. for 24 hours. The mixture was evaporated, the residue dissolved in water (5 ml) and washed with dichloromethane (10 ml). The aqueous solution was basified with 2M sodium hydroxide and extracted with dichloromethane (2×5 ml). The extracts were dried, filtered and evaporated to give the free base of the title product as an oil (0.20 g). The hydrochloride salt was prepared by adding ethanolic hydrogen chloride to an ethanol solution of the free base. Evaporated and the solid residue was recrystallised from ethanol (4 ml) to give the title product as a white solid, m.p. 215°–221° C.)

EXAMPLE 4

N,N'-Bis(3-aminopropyl)-5-methyl-2-(8-phenyloctyloxy)-1,3-benzenedimethanamine, tetrahydrochloride i) A solution of 5-methyl-2-(8-phenyloctyloxy)-1,3-benzene dicarboxaldehyde (1.75 g, 5 mmol) and N-tert.butoxycarbonyl-3-aminopropanamine (1.75 g, 10 mmol) in methanol (25 ml) was heated under reflux for 2 hours. After cooling to room temperature, sodium borohydride (1.14 g, 30 mmol) was added portionwise to the stirred solution over 45 minutes. The mixture was stirred overnight and then evaporated to a white residue. Water followed by 5M hydrochloric acid was added and the mixture was extracted twice with ether. The aqueous solution was basified with 5M sodium hydroxide and the product was extracted into dichloromethane. The dichloromethane was washed, dried and evaporated to give an oil (3 g). The product was purified by chromatography on flash silica, eluting with methanol then 5% 0.880 ammonia in methanol to give N,N'-bis(N-tert.butoxycarbonyl-1-3-aminopropyl)-5-methyl-2(8-phenyloctyloxy)-1,3-benzenedimethanamine as an oil (MS: M+H+ =669).

ii) The above oil (0.5 g, 0.8 mmol) was dissolved in ethanol (10 ml) and 3M ethanolic hydrogen chloride (4 ml) was added. After stirring for 4 days, the solution was evaporated to an oil which, on adding ethanol then ether, gave the title product as white crystals, m.p. 183°–185° C.

EXAMPLE 5

N,N'-Bis-(3-guanidinopropyl)-5-methyl-2-(8-phenyloctyloxy)-1,3-benzenedimethanamine, dinitrate A solution of N,N'-bis(3-aminopropyl)-5-methyl-2-(8-phenyloctyloxy)-1,3-benzenedimethanamine (0.29 g, 0.62 mmol) and 3,5-dimethylpyrazole carboxamidine, nitrate (0.25 g, 1.25 mmol) in 95% ethanol (10 ml) was heated at reflux. After one day, the solution was evaporated to an oil, water was added then the solution was extracted with ether three times. The aqueous solution was evaporated to give the title product as an oil (MS (FAB) M+H+ =553).

EXAMPLE 6

N,N'-Bis-(3-dimethylaminopropyl)-2-(9-phenylnonyl)-1,3-benzenedimethanamine, tetrahydrochloride i) A mixture of 8-phenyloctyl chloride (4.4 g), sodium iodide (5.34 g) and acetone (20 ml) was heated under reflux for 20 hours. Evaporated, water (20 ml) added and extracted with diethyl ether (20 ml). The extracts were dried, filtered and evaporated to a pale yellow liquid (5.5 g). Distilled to give 8-phenyloctyl iodide, b.p. 200° C. (air bath temperature) at 0.1 mBar.

ii) A solution of lithium diisopropylamide 1.5M in tetrahydrofuran (6 ml, 9 mmol) was added dropwise to a stirred solution of 2,6-dicyanotoluene (0.85 g, 6 mmol) and tetramethyl ethylenediamine (1.04 g, 9 mmol) in dry tetrahydrofuran (50 ml), cooled to −70° C. under nitrogen. After one hour, 8-phenyloctyl iodide (2.15 g, 6.8 mmol) was added dropwise at −70° C. to the intense blue suspension, then allowed to warm to 0° C. over one hour. Water (100 ml) was added (cautiously at first) to the brown mixture and then extracted with diethyl ether (50 ml). The extracts were washed with 2M hydrochloric acid, dried, filtered and evaporated to a brown oil (2.67 g). Purified by chromatography on flash silica eluting with dichloromethane gave 2-(9-phenylnonyl)-1,3-benzenedicarbonitrile as an oil.

iii) A solution of diisobutylaluminium hydride in toluene (3.1 ml, 4.6 mmol) was added dropwise to a stirred solution of 2-(9-phenylnonyl)-1,3-benzenedicarbonitrile (0.70 g, 2.1 mmol) in dry toluene (30 ml) under nitrogen, cooled in an ice bath. After one hour at room temperature methanol (1 ml) was added cautiously, followed by methanol:water (1:1, 1 ml) and 5M hydrochloric acid (15 ml). The mixture was extracted with diethyl ether (20 ml) and the extracts dried, filtered and evaporated to a yellow oil (0.8 g). Chromatography on flash silica eluting with dichloromethane gave 2-(9-phenylnonyl)-1,3benzenedicarboxaldehyde as a colourless oil.

iv) A mixture of dimethylaminopropamine (0.17 g, 1.7 mmol) and 2- (9-phenylnonyl)-1,3-benzenedicarboxaldehyde (0.26 g, 0.77 mmol) in methanol (5 ml) was heated under reflux for 2 hours. Solid sodium borohydride (0.19 g, 5 mmol) was added portionwise under nitrogen at room temperature and the mixture stirred overnight. Evaporated and water (10 ml) added to the residue, followed by extraction with dichloromethane (2×10 ml). The extracts were dried, filtered and evaporated to a colourless oil (0.31 g). Chromatography on flash silica eluting with 2% 0.880 ammonia in methanol gave the free base of the title product as an oil. The hydrochloride salt was prepared in ethanol solution with ethanolic hydrogen chloride, precipitated by the addition of diethyl ether and dried to give the title product as a white foam (MS: M+H+ =509).

EXAMPLE 7

N,N'-Bis(3-dimethylaminopropyl)-5-chloro-2-(8-phenyloctyloxy)1,3-benzenedimethanamine, tetrachloride 1) A mixture of 2,6-diformyl-4-chlorophenol (1.0 g, 5.4 mmol), 8-phenyloctyl chloride (1.35 g, 6 mmol) and anhydrous potassium carbonate (0.83 g, 6 mmol) in dry dimethylformamide was heated to 140° C. for 6 hours. After cooling to room temperature, water (29 ml) was added and the mixture extracted with ethyl acetate (20 ml). The extracts were washed with 2M sodium hydroxide (2×10 ml), water (10 ml), dried, filtered and evaporated to a brown oil. Chromatography on flash silica eluting with diethyl ether gave 5-chloro-2-(8-phenyloctyloxy)-3-benzenedicarboxaldehyde as a pale yellow oil (2 g).

ii) The title product was prepared from 5-chloro-2-(8-phenyloctyloxy)-1,3-benzenedicarboxaldehyde using the method described in Example 2 and recrystallised from ethanol-diethyl ether as white solid, m.p. 196°–198° C.

EXAMPLE 8

N,N'-Bis(3-dimethylaminopropyl)-5-methyl-2-[6-(benzylthio hexyloxy]-1,3-benzenedimethanamine, tetrahydrochloride i) A mixture of 5-methyl-2-hydroxy-1,3-benzenedicarboxaldehyde (2.46 g, 15 mmol), dibromohexane (11.0 g, 45 mmol) and potassium carbonate (2.76 g, 20 mmol) in dry dimethylformamide (50 ml) was heated to 80° C. for 1 hour. To the cooled mixture, water (100 ml) and diethyl ether (50 ml) were added. Insoluble solid was filtered. The ether solution was washed with 2M sodium hydroxide (50 ml), water (50 ml), dried, filtered and evaporated to a pale liquid (12.8 g). Excess dibromohexane was removed by distillation (200° C. at 10 mmol) and the residue crystallised from cyclohexane (20 ml) to give 2-(6-bromohexyloxy)-5-methyl-1,3benzenedicarboxaldehyde, m.p. 46° C.

ii) A solution of sodium ethoxide (69 mg sodium, 3 mmol in ethanol 1 ml) was added to a stirred suspension of 2-(6-bromohexyloxy)-5-methyl-1,3-benzenedicarboxaldehyde (0.98 g, 3 mmol) and benzyl mercaptan (0.35 g, 3 mmol) in ethanol (10 ml) at room temperature under nitrogen. After 1 hour evaporated, water (10 ml) and 2M sodium hydroxide (2 ml) added and extracted with diethyl ether (10 ml). The extracts were washed with water, dried, filtered and evaporated to an oil (1.12 g). Chromatography on silica eluting with dichloromethane gave 2-(6-benzylthiohexyloxy)-5-methyl-1,3-benzenedicarboxaldehyde as a colourless oil.

iii) The title product was prepared from 2-(6-benzylthiohexyloxy)-5-methyl-1,3-benzenedicarboxaldehyde using the method described in Example 2 as a colourless hydroscopic glass (MS: $M+H^+ = 543$).

EXAMPLE 9

N,N'-Bis(3-dimethylaminopropyl)-5-methyl-2-[8-(4-methylphenyl)octyloxy-1,3-benzenedimethanamine tetrahydrochloride i) Lithium chloride (0.15 g, 3.5 mmol) and cupric chloride (0.3 g, 2.2 mmol) were added to THF (100 ml) and stirred for 1 hour 30 minutes. 1,8-Dibromooctane (37 g, 137 mmol) was then added. While keeping the temperature between 0° C. and 5° C., 4-methylphenyl magnesium bromide in THF (prepared from magnesium (2.3 g, 95 mmol) and 4-methylphenyl bromide (15.4 g, 90 mmol) in THF (150 ml)) was added over 1 hour, allowing the temperature to reach room temperature overnight. The reaction mixture was poured over concentrated hydrochloric acid/ice mixture and the product was extracted into ether. The ether was washed with saturated sodium chloride solution, dried over anhydrous magnesium sulphate and evaporated to give an oil, which was distilled under vacuum to give 8-(4-methylphenyl)octylbromide as an oil, bp 128° at 0.2mm.

ii) 5-Methyl-2-[8-(4-methylphenyl)octyloxy]-1,3-benzenedicarboxaldehyde was prepared from 8-(4-methylphenyl)octyl bromide using the method described in Example 1 as an oil.

iii) The title product was prepared from 5-methyl-2-[8-(4-methylphenyl)octyloxy]-1,3-benzenedicarboxaldehyde by the method described in Example 2 as a solid, m.p. 175°–178° C.

EXAMPLE 10

N,N'-Bis(3-dimethylaminopropyl)-5-methyl-2-[8-(4-chlorophenyl)-octyloxy]1,3-benzenedimethanamine tetrahydrochloride i) 8-(4-Chlorophenyl)octyl bromide was prepared from 4-chlorophenyl magnesium bromide using the method described in Example 9 (i) as a colourless liquid, b.p. 128° C. at 0.15 mm.

ii) 5-Methyl-2-[8-(4-chlorophenyl)octyloxy]-1,3-benzenedicarboxaldehyde was prepared from 8-(4-chlorophenyl)octyl bromide using the method described in Example 1 as an oil.

iii) The title product was prepared from 5-methyl-2-[8-(4-chlorophenyl)-octyloxy]-3-benzenedicarboxaldehyde using the method in Example 2 as a solid, m.p. 150°–152° C.

EXAMPLE 11

N,N'-Bis(3-dimethylaminopropyl)-5-methyl-2-[8-(4-methoxyphenyl)octyloxy]-1,3-benzenedimethanamine. tetrahydrochloride i) 8-(4-Methoxyphenyl)octyl bromide was prepared from 4-methoxyphenyl magnesium bromide using the method in Example 9 (i) as a colourless liquid, b.p. 126° C. at 0.15 mm.

ii) 5-Methyl-2-[8-(4-methoxyphenyl)octyloxyl]-1,3-benzenedicarboxaldehyde was prepared from 8-(4-methoxyphenyl)octyl bromide using the method described in Example 1 as an oil.

iii) The title product was prepared from 5-methyl-2-[8-(4-methoxyphenyl)octyoxy]-1,3-benzenedicarboxaldehyde using the method in Example 2 as a solid 167°–172° C.

EXAMPLE 12

N,N'-Bis(3-dimethylaminopropyl)-5-methyl-2-(6-phenylhexyloxy)-1,3-benzenedimethanamine tetrahydrochloride i) 5-Methyl-2-(6-phenylhexyloxy)-1,3-benzenedicarboxaldehyde (m.p. 64° C.)was prepared from 6-phenylhexyl chloride using the method described in Example 1 at a higher reaction temperature of 120° C.

ii) The title product was prepared from 5-methyl-2-(6-phenylhexyloxy)-1,3-benzenedicarboxaldehyde using the method in Example 2 as a hydroscopic glass (MS: $M+H^+ = 497$).

EXAMPLE 13

N,N'-Bis(3-dimethylaminompropyl)-5-methyl-2-[8(4-hydroxyphenyl)octyloxy]-3-benzenedimethanamine tetrahydrochloride i) A 1M solution of boron tribromide in dichloromethane (5 ml, 5 mmol) was added to an ice water cooled solution of 8-(4-methoxyphenyl)octylbromide (1.5 g, 5 mmol) in dichloromethane (10 ml). After 4 hours at room temperature, water was added and the dichloromethane separated, washed with water, dried over anhydrous magnesium sulphate, and evaporated to give an oil, which was chromatographed over flash silica, eluting with chloroform, followed by 2% methanol in chloroform to give 8-(4-hydroxyphenyl)octylbromide as an oil (MS: $M^+ = 284$).

ii) 50% sodium hydride in an oil dispersion (0.185 g, 3.85 mmol) was added to 8-(4-hydroxyphenyl) octylbromide (1.1 g, 3.85 mmol) in THF (30 ml) with ice cooling. After 1 hour, methoxyethoxymethyl chloride (0.48 g, 3.85 mmol) in THF (2 ml) was added and the mixture was stirred for five days. Water was added and the excess THF evaporated off. After the addition of more water, the product was extracted into dichloromethane. The dichloromethane was washed with water, dried over anhydrous magnesium sulphate and evaporated to give an oil (1.5 g), which was chromatographed over a column of flash silica, eluting with chloroform to give 8-(4-methoxyethoxymethoxyphenyl)octylbromide as an oil (MS: $M^+ = 372$).

iii) 5-Methyl-2-[8- (4-methoxyethoxymethoxyphenyloctyloxy]-1,3-benzenedicarboxaldehyde (MS: $M^+ = 456$) was prepared from 8-(4-methoxyethoxymethoxyphenyl) octylbromide using the method described in Example 1.

iv) Zinc bromide (1.4 g, 6.2 mmol) was added in one lot to 5-methyl-2-[8-(4-methoxyethoxymethoxyphenyl-)octyloxy]-1,3-benzenede-carboxaldehyde (1.31 g, 3.2 mmol) in dichloromethane (20 ml). After stirring at room temperature for 1 hour 45 minutes, water was added and the product was extracted into dichloromethane. The dichloromethane was washed, dried and evaporated to give an oil, which was purified on flash silica, eluting with increasing amounts of methanol (1%, 2%, 5%) in dichloromethane to give 5-methyl-2-[8-(4-hydroxyphenyl)octyloxy]-1,3-benzenedicarboxaldehyde as an oil (MS: $M^+ = 368$).

v) The title product was prepared from 5-methyl-2-[8-(4hydroxyphenyl)octyloxy]-1,3-benzenedicarboxaldehyde using the method in Example 2 as an oil (MS: $M+H^+ = 542$).

EXAMPLE 14

N,N'-Bis(3-dimethylaminopropyl-2-[4-fluorophenyl)-butyloxy]-5-methyl-1,3-benzenedimethanamine tetrahydrochloride i) 2-[4-bis(4-fluorophenyl)butyloxy-5-methyl -1,3-benzenedicarboxaldehyde (m.p. 97° C.) was prepared from 1,1'-(4-chlorobutylidene)bis(4-fluorobenzene) using the method described in Example 1 at a higher reaction temperature of 150° C.

ii) The title product was prepared from 2-[4-bis(4-fluorophenyl)-butyloxy-5-methyl-1,3-benzenedicarboxaldehyde using the method in Example 2 and the solid recrystallised from ethanol-diethyl ether, m.p. 162°-164° C.

EXAMPLE 1

N,N'-Bis(3-dimethylaminopropyl)-4-(8-phenyloctyloxy)-1,3-benzenedimethanamine tetrahydrochloride i) 4-(8-Phenyloctyloxy)-3-benzenedicarboxaldehyde (m.p.55° C., isopropanol) was prepared from 4-hydroxy-3-benzenedicarboxaldehyde using the method in Example 1.

ii) The title product was prepared from 4-(8-phenyloctyloxy)-1,3-benzenedicarboxaldehyde using the method in Example 1 and the solid recrystallised from ethanol-diethyl ether, m.p. 109°-113° C.

EXAMPLE 16

N,N'-Bis(3-dimethylaminopropyl-4-(6-phenylhexyloxy)-1,3-benzenedimethanamine tetrahydrochloride i) 4-(6-phenylhexyloxy)-1,3-benzenedicarboxaldehyde was prepared from 4-hydroxy-1,3-benzenedicarboxaldehyde and 6-phenylhexyl chloride using the method in Example 1 at a higher reaction temperature of 140° C.

ii) The title produce was prepared from 4-(6-phenylhexyloxy)-1,3-benzenedicarboxaldehyde using the method in Example 2 as a hydroscopic solid (MS: $M+H = 483$).

EXAMPLE 17

N,N'-Bis(3-aminopropyl)-4-(6-phenylhexyloxy)-1,3-benzenedimethanamine tetrahydrochloride i) N,N'-bis(N-tert.butoxycarbonyl-3-amino propyl)-4-(6-phenylhexyloxy)-1,3-benzenedimethanamine (MS: $M+H^+ = 627$) was prepared from 4-(6-phenylhexyloxy)-1,3-benzenedicarboxaldehyde and N-tert.butoxycarbonyl-3-aminopropanamine using the method in Example 2.

ii) The title product was made as an amorphous solid from N,N'-bis(N-tert.butoxycarbonyl-3-aminopropyl)-4-(6-phenylhexyloxy)-1,3-benzenedimethanamine (MS: $M+H^+ = 427$) using the method in Example 4 (ii).

EXAMPLE 18

N,N'-Bis(3-dimethylaminopropyl)-4-[6- (biphenyl-4-yl) hexyloxy]-1,3-benzenedimethanamine tetrahydrochloride i) 6-(Biphenyl-4-yl)hexanoic acid methyl ester (0.67 g, 2.4 mmol) in THF (5 ml) was added dropwise to lithium aluminium hydride (0.2 g, 5.3 mmol) in THF cooled to 0° C. After stirring for 1 day at room temperature, water (1 ml) then 5M sodium hydroxide (1 ml) followed by water (2 ml) were added cautiously followed by stirring at room temperature for 2 hours. The precipitate was filtered off and filtrate was evaporated to give 6-(biphenyl-4-yl)hexanol as a solid (MS: $M^+ = 254$).

ii) p-Toluenesulphonyl chloride (1 g, 5.2 mmol), was added portionwise to a stirred solution of 6-(biphenyl-4-yl)hexanol (1.5 g, 4.8 mmol), pyridine (0.42 g, 5.2 mmol) in dichloromethane (10 ml). After stirring for 2 days, the solution was evaporated to dryness. Water, then 5M sodium hydroxide was added and the product was extracted into dichloromethane. The dichloromethane was washed, dried and evaporated to give an oil (2.2 g). The oil was purified by chromatography on silica, eluting with dichloromethane to give 6-(biphenyl-4-yl)hexyl tosylate as an oil (1.46 g, 75%).

iii) 4-[6-(biphenyl-4-yl)hexyloxy]-1,3-benzenedicarboxaldehyde (MS: $M+NH_4^+ = 400$) was prepared from 5-formyl salicylaldehyde and 6-(biphenyl-4-yl)hexyl tosylate at a temperature of 150° C. using the method in Example 1.

iv) The title product (m.p. 129°-131° C.) was made as a white crystalline salt from 4-[6-(biphenyl-4-yl)hexyloxy]-1,3-benzenecarboxaldehyde using the method in Example 2.

EXAMPLE 19

N,N'-Bis(3-dimethylaminopropyl)-4-[4-(9,10-dihydro-2-phenanthryl)butoxy]-1,3-benzendimethanamine tetrahydrochloride i) 4-(9,10-Dihydro-2-phenanthryl)butanol (MS: $M+NH_4^+ = 270$) was prepared from 4-(9,10-dihydro-2-phenanthryl)butyric acid using the method in Example 18 (i).

ii) 4-(9,10-Dihydro-2-phenanthryl)butyl tosylate (MS: $M+NH_4^+ = 424$) was prepared from 4-(9,10-dihydro-2-phenanthryl)butyric acid using the method in Example 18 (ii).

iii) 4-[-4-(9,10-Dihydro-2-phenanthryl)butoxy]-1,3-benzene dicarboxaldehyde (m.p. 116° C.) was made from 4-(9,10-dihydro-2-phenanthryl)butyl tosylate using the method in Example 1.

iv) The title product was made from 4-[-4-(9,10-dihydro-2-phenanthryl)butoxy]-1,3-benzene dicarboxaldehyde as a white crystalline salt (m.p. 148°-150° C.) using the method in Example 2.

EXAMPLE 20

N,N'-Bis(3-dimethylaminopropyl) -2,5-dimethyl-4-(8-phenyloctyloxy)-1,3-benzenedimethanamine tetrahydrochloride i) 2,5-Dimethyl -4-(8-phenyloctyoxy)-1,3-benzenedicarboxaldehyde (MS: $M+H^+ = 367$) was made from 8-phenyloctylchloride and 2,5-dimethyl-4-hydroxybenzenedicarboxaldehyde and at a temperature of 100° C., using the method in Example 1.

ii) The title product was made from 2,5-dimethyl-4-(8-phenyloctyoxy-1,3-benzedicarboxaldehyde as an amorphous solid (m.p. 143°-148° C.) using the method in Example 2.

EXAMPLE 21

N,N'-Bis(3-dimethylaminopropyl)-5-methoxy-4-(6-phenylhexyloxy)-1,3-benzenedimethanamine tetrahydrochloride i) A mixture of dimethyl 4-hydroxy-5-methoxy benzene-1, 3-dicarboxylate, (2.4 g, 10 mmol), potassium carbonate (1.5 g, 11 mmol), 6-phenylhexylchloride (2 g, 10.2 mmol), potassium iodide (1.7 g, 10.1 mmol), and DMF (50 ml) was heated with stirring at 100° C. for 1 day. After evaporation, water was added to the residue and the product extracted into dichloromethane. The dichloromethane was washed with water, dried over magnesium sulphate and evaporated to give an oil (4.2 g). The product was purified by chromatography on flash silica, eluting with chloromethane to give dimethyl 5-methoxy-4-(6-phenylhexyloxy)benzene-1,3-dicarboxylate, MS: $M+H^+=401$) as an oil.

ii) A solution of dimethyl 5-methoxy-4-(6-phenylhexyloxy)benzene-1,3-dicarboxylate (3.4 g, 8.6 mmol) and sodium hydroxide (3.4 g, 85 mmol) in water (50 ml) and methanol (50 ml) was refluxed overnight. After evaporation, water was added to the residue and the solution was extracted with ether. The solution was acidified with 5M hydrochloric acid and the product was extracted in dichloromethane. The dichloromethane was washed with water, dried over anhydrous magnesium sulphate and evaporated to give 5-methoxy-4-(6-phenylhexyloxy)benzene-3-dicarboxylic acid, m.p. 113°-115° C. (ethanol).

iii) Triethylamine (0.29 g, 2.9 mmol) and ethyl chloroformate (0.31 g, 2.9 mmol) were added to a solution of 5-methoxy-4-(6-phenylhexyloxy)benzene-1, 3-dicarboxylic acid (0.53 g, 1.42 mmol) in dichloromethane (20 ml). After 1 hour 30 minutes, 3-dimethylaminopropylamine (0.3 g, 2.9 mmol) was added and the mixture was stirred for 1 day. Water then 5M sodium hydroxide solution was added and the product was extracted into dichloromethane. The dichloromethane was washed with water, dried over anhydrous magnesium sulphate and evaporated to give an oil, which was chromatographed on flash silica, eluting with 5% 0.880 ammonia in methanol to yield N,N'-bis-(3-dimethylaminopropyl)-5-methoxy-4-(6-phenylhexyloxy)benzene-1,3-dicarboxamide as an oil, MS: $M+H=541$).

iv) N,N'-Bis-(3-dimethylaminopropyl)-5-methoxy-4-(6-phenylhexyloxy)benzene-1,3-dicarboxamide (0.25 g, 0.46 mmol) in THF (10 ml) was added to lithium aluminium hydride (0.036 g, 0.95 mmol) in THF (5 ml) at 0° C. After refluxing for 2 hours, more lithium aluminium hydride (0.72 g, 19 mmol) in THF [2 ml] was added and the mixture was refluxed for 4 days. Water, then 5M sodium hydroxide, was added and the product was extracted into ether. The ether was washed with water, dried over anhydrous magnesium sulphate and evaporated to give an oil, which was purified on flash silica, eluting with methanol the successive amounts of 0.880 ammonia (1%, 2%, 5%) in methanol to give the free base of title product as an oil (MS: $M+H^+=513$).

EXAMPLE 2

N,N'-Bis(3-dimethylaminopropyl)-5-(6-phenylhexyloxy)-1,3-benzenedimethanamine tetrahydrochloride i) Dimethyl 5-(6-phenylhexyloxy)benzene-1,3-dicarboxylate was made from dimethyl 5-hydroxybenzene-1,3-dicarboxylate and 6-phenylhexylchloride using the method in Example 21(i).

ii) 5-(6-phenylhexyloxy)benzene-1,3-dicarboxylic (m.p. 204°-205° C.) was made from dimethyl 5-(6-phenylhexyloxy)benzene-1,3-dicarboxylate using the method in Example 21(ii).

iii) N,N'-Bis-(3-dimethylaminopropyl)-5-(6-phenylhexyloxy)benzene-1,3-dicarboxamide was made from 5-(6-phenylhexyloxy)-1,3-dicarboxylic acid (MS: $M+H=511$) using the method in Example 21 (iii).

iv) The title product was made from N,N'-bis(3-dimethylaminopropyl)-5-(6-phenylhexyloxy)benzene-1,3-dicarboxamide as an oil using the method in Example 21(iv) (MS: $M+H=483$).

EXAMPLE 23

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 24

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatin capsules in 200 mg quantities.

We claim:

1. A compound of the formula:

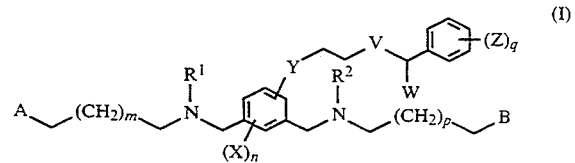

-continued in which A is 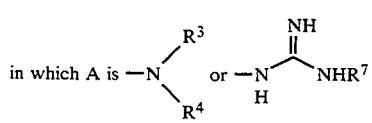

B is 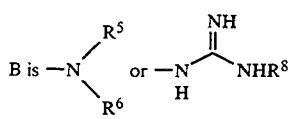

$R^1$ to $R^8$ are each hydrogen or $C_{1-4}$ alkyl, m, n and p are each 0, 1, or 2, q is 0, 1, 2 or 3, X and Z are each $C_{1-4}$ alkyl, $C_{1-4}$ alkoxy, hydroxy, nitro, cyano, halo, trihalomethyl, carboxy, $C_{1-4}$ alkoxy-carbonyl or phenyl, and in addition Z, together with the phenyl ring to which it is attached, can be:

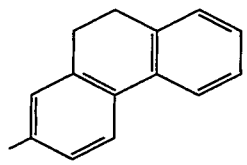

Y is —O—, —S— or —CH$_2$—, V is —(CH$_2$)$_r$— or —(CH$_2$)$_r$S— where r is 1 to 15, and W is hydrogen or optionally substituted phenyl; and salts thereof.

2. A compound according to claim 1, in which A and B are —NR$^3$R$^4$ and —NR$^5$R$^6$ respectively, and R$^3$, R$^4$, R$^5$ and R$^6$ are each hydrogen or methyl.

3. A compound according to claim 2, in which R$^1$ and R$^2$ are both hydrogen, and m and p are 1.

4. A compound according to claim 3, in which n is 0 or 1, Y is —O—, V is —(CH$_2$)$_r$—, and W is hydrogen.

5. A pharmaceutical formulation comprising a compound according to claim 1, or a pharmaceutically-acceptable salt thereof, together with a pharmaceutically-acceptable diluent or carrier therefor.

* * * * *